United States Patent [19]

Della Corna et al.

[11] Patent Number: 4,955,899
[45] Date of Patent: Sep. 11, 1990

[54] LONGITUDINALLY COMPLIANT VASCULAR GRAFT

[75] Inventors: Linda V. Della Corna, Glendale; Robert C. Farnan, Tucson; William M. Colone, Phoenix; Rajagopal R. Kowligi, Tempe, all of Ariz.

[73] Assignee: Impra, Inc., Tempe, Ariz.

[21] Appl. No.: 358,787

[22] Filed: May 26, 1989

[51] Int. Cl.⁵ .......................... A61F 2/06; A01N 1/02
[52] U.S. Cl. ......................................... 623/1; 623/12; 623/901; 427/2
[58] Field of Search ................ 623/1, 11, 12, 901; 427/2

[56] References Cited

U.S. PATENT DOCUMENTS

| | | |
|---|---|---|
| Re. 31,618 | 7/1984 | Mano et al. .................. 623/1 |
| 3,279,996 | 10/1966 | Long et al. .................. 623/2 X |
| 3,479,670 | 11/1969 | Medell .......................... 623/1 |
| 3,585,647 | 6/1971 | Gajewski et al. ............ 623/1 |
| 4,011,861 | 3/1977 | Enger ...................... 128/419 P X |
| 4,173,689 | 11/1979 | Lyman et al. ................ 521/64 |
| 4,187,390 | 2/1980 | Gore ......................... 174/102 R |
| 4,193,138 | 3/1980 | Okita ............................ 623/1 |
| 4,194,041 | 3/1980 | Gore et al. .................. 428/315 |
| 4,208,745 | 5/1980 | Okita ............................ 623/1 |
| 4,304,010 | 12/1981 | Mano ............................ 623/1 |
| 4,306,318 | 12/1981 | Mano et al. ................... 623/1 |
| 4,321,711 | 3/1982 | Mano ............................ 623/1 |
| 4,344,999 | 8/1982 | Gohlke ....................... 428/212 |
| 4,355,426 | 10/1982 | MacGregor .................. 623/1 |
| 4,377,010 | 4/1983 | Fydelor et al. ............... 623/1 |
| 4,441,215 | 4/1984 | Kaster .......................... 623/1 |
| 4,657,544 | 4/1987 | Pinchuk ....................... 623/1 |
| 4,718,907 | 1/1988 | Karwoski et al. ............ 623/12 |
| 4,743,258 | 5/1988 | Ikada et al. ................... 623/1 |
| 4,816,339 | 3/1989 | Tu et al. ..................... 428/421 |

FOREIGN PATENT DOCUMENTS

0157178 10/1985 European Pat. Off. .
2077107A 12/1981 United Kingdom .................... 623/1

OTHER PUBLICATIONS

*An in vitro Study of the Properties Influencing Staphylococcus Epidermidis Adhesion to Prosthetic Vascular Graft Materials*, Joel M. Harris, M. D. and Louis F. Martin, M. D., Ann. Surg., Nov., 1987, pp. 612-619.
Promotional Literature for "Tecoflex" by Thermedics, Inc., Tecoflex Solution Processible Grades, 470 Wildwood St., Woburn, MA.
Kenney et al., "Evaluation of Compliant and Noncompliant PTFE Vascular Prostheses", *Trans Am. Soc. Artif. Intern. Organs*, vol. XXXIV, 1988, pp. 661–663.
Shu et al., "Flow Phenomena in Compliant and Noncompliant Arterioenous Grafts", *Trans. Am. Soc. Artif. Intern. Organs*, vol. XXXIV, 1988, pp. 519–523.

*Primary Examiner*—Ronald Frinks
*Attorney, Agent, or Firm*—Cahill, Sutton & Thomas

[57] ABSTRACT

A longitudinally compliant PTFE graft is provided by compressing at least a portion of a porous PTFE tube along its longitudinal axis and coating at least the outer wall of the compressed portion of the PTFE tube with a biocompatible elastomer for allowing the compressed portion of the tube to be stretched along the longitudinal axis. The PTFE tube is compressed by pulling the tube over a cylindrical mandrel of like diameter and applying a compression force to the tube along its longitudinal axis. The compressed portion(s) is (are) secured against movement upon the mandrel, and a coating of liquified polyurethane or other biocompatible elastomer is then applied over at least the compressed portion(s) of the tube. The elastomeric coating may be applied by dip coating or spray coating techniques. After the elastomeric coating has dried, the completed graft is removed from the mandrel.

19 Claims, 3 Drawing Sheets

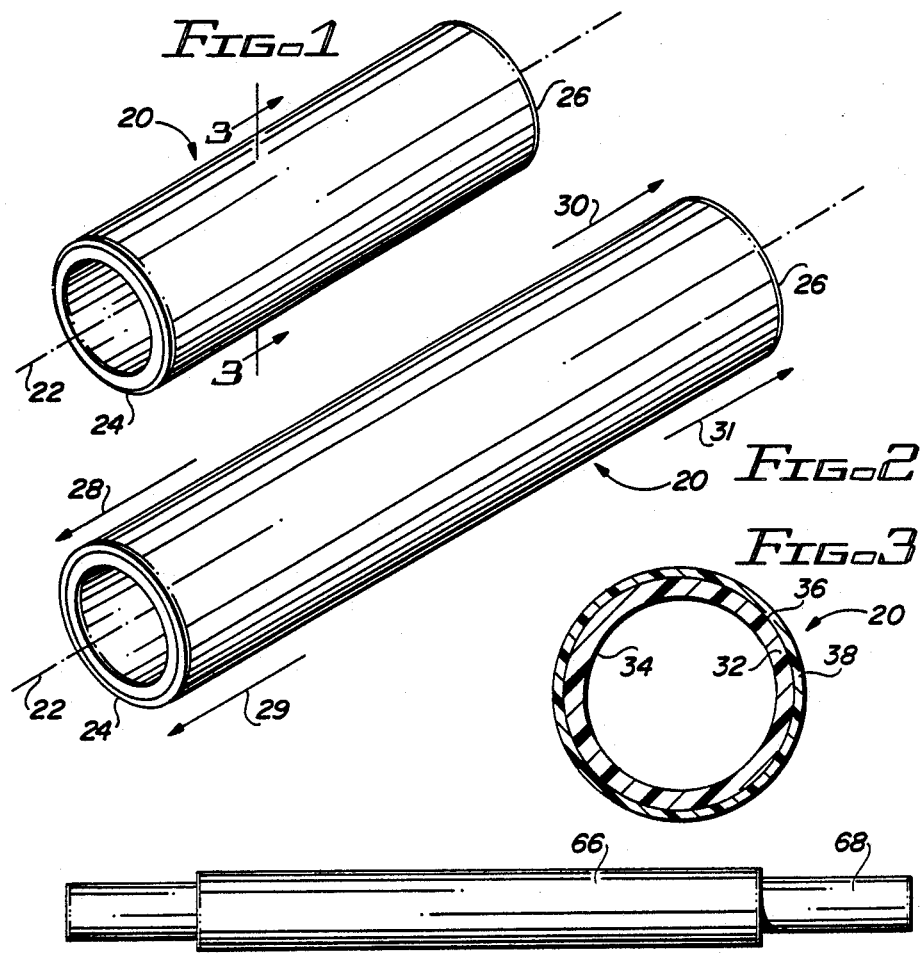

LONGITUDINALLY COMPLIANT VASCULAR GRAFT

CROSS-REFERENCE TO RELATED PATENT APPLICATIONS

1. "BLOOD VESSEL PATCH", Ser. No. 07/358,785, filed concurrently herewith, naming Berguer et al. as inventors, and assigned to the assignee of the present invention.

2. "NON-POROUS COATED PTFE GRAFT", Ser. No. 07/358,011, filed concurrently herewith, naming Kowligi et al. as inventors, and assigned to the assignee of the present invention.

BACKGROUND OF THE INVENTION

1. Field of the Invention

The present invention relates generally to prosthetic vascular grafts for implantation within the vascular system of a patient, and more particularly, to a prosthetic vascular graft made from expanded, porous polytetrafluorethylene (PTFE) tubing that is fabricated to be longitudinally compliant for allowing at least a portion of the PTFE graft to be stretched along the longitudinal axis thereof.

2. Description of the Prior Art

The use of implantable prosthetic vascular grafts made of expanded, porous PTFE is well known in the art. Such vascular grafts are often implanted just below the skin to provide blood access for long term hemodialysis. Such PTFE vascular grafts are also used to replace or bypass occluded or damaged natural blood vessels. Such prosthetic vascular grafts, and methods of implanting the same, are generally described in Bennion et al., "Hemodialysis and Vascular Access", Vascular Surgery. pp. 625–662, 1983. Methods of forming expanded, porous PTFE tubing are well known in the art. For example, U.S. Pat. No. 4,187,390 issued to Gore discloses one such process which may be used to produce highly porous, expanded PTFE structures.

Expanded, porous PTFE material offers a number of advantages when used as a prosthetic vascular graft. PTFE is highly biocompatible, has excellent mechanical and handling characteristics does not require preclotting with the patient's blood, heals relatively quickly following implantation, and is thromboresistant. Notwithstanding its many advantages, certain problems may arise with the use of PTFE vascular grafts. For example, PTFE material is not very elastic, and the suture holes formed in the ends of the graft when the graft is sutured to a blood vessel during implantation often leak blood until clotting occurs Within the suture holes. Moreover, in those instances when a PTFE vascular graft is implanted below the skin for being cannulated by a hemodialysis needle, the vascular graft must be tunneled under the skin between the artery and vein to which the graft is to be anastomosed. Occasionally, a surgeon will misjudge the length of the graft that is required to reach between the selected artery and vein; in these situations, the surgeon may find that the graft is too short to reach the targeted site once the graft has been tunnelled under the skin. PTFE vascular grafts typically exhibit minimal longitudinal compliance, and hence the graft may not be stretched significantly along its longitudinal axis. Accordingly, in such cases, the surgeon must then remove the tunnelled graft from below the skin and repeat the tunneling procedure with a longer graft.

As mentioned above, PTFE vascular grafts are often used to provide a bypass within the vascular system. Two examples of the use of PTFE vascular grafts as bypass implants include an axillofemoral bypass graft, wherein the vascular graft extends between the femoral artery in the upper leg to the axillary artery in the shoulder, as well as a femoropopliteal bypass graft extending below the knee. Such bypass grafts often place restrictions upon the freedom of movement of the patient in order to avoid pulling the graft loose from its anchor points. For example, in the case of the axillofemoral bypass graft, sudden or extreme movements of the arm or shoulder must be entirely avoided. Similarly, in the case of the femoropopliteal bypass graft, bending the knee can place dangerous stress upon the graft. The above-described restricted movement is due largely to the inability of the PTFE vascular graft to stretch along its longitudinal axis when its associated anchor points are pulled apart from one another. Such restrictive movement is especially important during the early period of healing following implantation When there is still little tissue incorporation into the graft and it can move within the subcutaneous tunnel.

Furthermore, some medical studies have suggested that vascular graft compliance may play an important role in graft failure. These studies make note of the mechanical mismatch created by surgical anastomoses, due in part to the inability of PTFE vascular grafts to exhibit any longitudinal or radial compliance. In this regard, see generally Shu et al., "Flow Phenomena In Compliant And Noncompliant Arteriovenous Grafts", *Trans Am Soc. Artif. Intern. Organs*, vol. XXXIV, 1988, pp. 519–523; and Kenney et al., "Evaluation of Compliant And Noncompliant PTFE Vascular Prostheses", *Trans Am Soc. Artif. Intern. Organs*, vol. XXXIV, 1988, pp. 661–663.

Accordingly, it is an object of the present invention to provide a PTFE prosthetic vascular graft which retains the advantages of using PTFE material as described above, but which is longitudinally compliant over at least a portion of its length for allowing the graft to be stretched along its longitudinal axis It is another object of the present invention to provide such a longitudinally compliant PTFE graft which minimizes suture hole bleeding at the ends of the graft at those points where the graft is anastomosed to blood vessels within the body.

It is still another object of the present invention to provide such a vascular graft which may be stretched along its longitudinal axis, and thereby make less critical the sizing of the graft prior to implantation.

It is a further object of the present invention to provide such a longitudinally compliant vascular graft which permits a patient greater freedom of movement and which minimizes the likelihood of the ends of the graft pulling loose from their associated anchor points when the graft is stretched due to movements of the patient's body.

These and other objects of the present invention will become more apparent to those skilled in the art as the description thereof proceeds.

SUMMARY OF THE INVENTION

Briefly described, and in accordance with a preferred embodiment thereof, the present invention relates to a longitudinally compliant PTFE vascular graft which includes a length of expanded, porous PTFE material in tubular form. It least a portion of the PTFE tube is initially compressed during manufacture of the longitudinally compliant graft, and a coating of a biocompatible elastomer, such as polyurethane, is applied over at least the compressed portion of the PTFE tube. The resulting PTFE tube, including the elastomeric coating formed upon the outer wall thereof, exhibits longitudinal compliance and may be stretched along the longitudinal axis of the tube within the portion of the tube that Was compressed prior to application of the elastomeric coating.

The PTFE tube may be compressed along its entire length prior to application of the elastomeric coating, in which case the resulting vascular graft exhibits longitudinal compliance over its entire length. Alternatively, the vascular graft may be constructed wherein only the end portions of the graft are initially compressed prior to application of the elastomeric coating, in which case the resulting vascular graft exhibits longitudinal compliance within its end portions only.

While polyurethane is the preferred elastomeric coating, other suitable elastomers include medical-grade silicone rubber elastomers, segmented polyurethanes, polyurethane-ureas, and silicone-polyurethanecopolymers.

The present invention also relates to the method by which such a longitudinally compliant PTFE vascular graft is produced. The preferred method includes the step of compressing the porous PTFE tube over at least a portion of its length while maintaining the internal diameter of the PTFE tube essentially constant. A coating of a liquified biocompatible elastomer is then applied to the outer cylindrical wall of the PTFE tube over at least the compressed portion thereof. As used herein, the term liquified elastomer should be understood to refer to an elastomer dissolved in a liquid solvent. The liquified elastomer coating is then dried while maintaining the compressed Portion of the PTFE tube in its compressed position.

Preferably, the PTFE tube is initially pulled over a supporting mandrel having an outer diameter that is equal to or slightly larger than the internal diameter of the PTFE tube before the PTFE tube is compressed. The mandrel aids in supporting the PTFE tube and in maintaining the internal diameter thereof constant, helps to maintain the compressed portion of the PTFE tube in its compressed state during further processing steps, and also helps to prevent the liquified elastomer from reaching the inner cylindrical wall of the PTFE tube. The liquified elastomer may be applied by any method which produces a controlled and uniform coating upon the outer cylindrical wall of the PTFE tube. Preferred coating methods include dip coating the PTFE tube and its supporting mandrel into a container of the liquified elastomer, as well as spraying the liquified elastomer upon the PTFE tube while the tube is supported by the mandrel.

BRIEF DESCRIPTION OF THE DRAWINGS

FIG. 1 is a perspective view of a longitudinally compliant PTFE vascular graft constructed in accordance with the teachings of the present invention, and shown in its initial unstretched condition.

FIG. 2 is a perspective view of the longitudinally compliant vascular graft shown in FIG. 1 while the same is being stretched outwardly along its longitudinal axis to demonstrate the longitudinal compliance of such graft.

FIG. 3 is a cross-sectional drawing of the vascular graft shown in FIG. 1 taken through the lines designated 3—3 Within FIG. 1.

FIG. 4 is a top view of a porous PTFE tube pulled onto a supporting mandrel before the PTFE tube is compressed.

FIG. 5 shows the PTFE tube and supporting mandrel of FIG. 4 while the PTFE tube is being compressed along its longitudinal axis.

FIG. 6 shows the PTFE tube and supporting mandrel of FIG. 5, along With anchoring Wires for retaining the PTFE tube in its compressed condition during further processing steps.

DETAILED DESCRIPTION OF THE PREFERRED EMBODIMENTS

Figure 7:
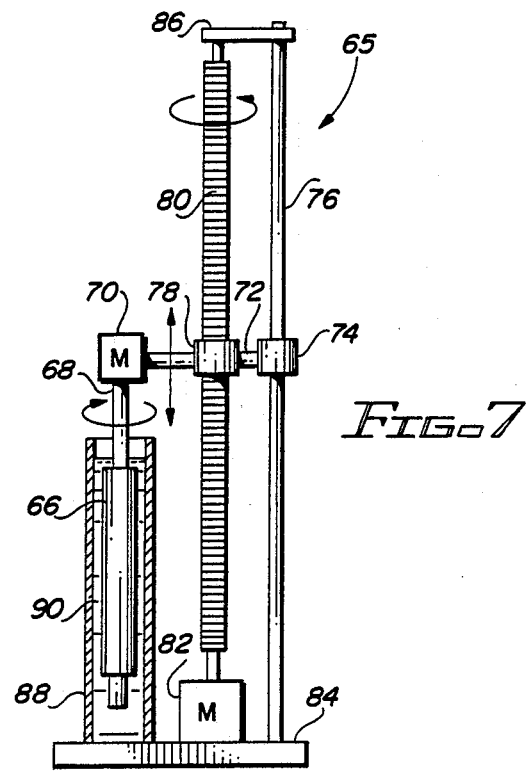
FIG. 7 is a front view of a dip coating apparatus adapted to apply a uniform elastomeric coating to the outer cylindrical wall of a compressed PTFE tube.

In FIG. 1, a longitudinally compliant PTFE vascular graft is designated generally by reference numeral 20. As shown, vascular graft 20 is in tubular form and may be made to have any desired length and internal diameter. Within FIG. 1, dashed lines 22 indicate the central longitudinal axis of vascular graft 20. Vascular graft 20 includes a first end 24 and an opposing second end 26.

In FIG. 2, vascular graft 20 of FIG. 1 is shown being stretched from its opposing ends 24 and 26 along longitudinal axis 22. Arrows 28 and 29 indicate that end 24 is pulled in a first direction along longitudinal axis 22, while arrows 30 and 31 indicate that opposing end 26 of vascular graft 20 is being pulled in the opposing direction. When the pulling forces designated by arrows 28-31 are removed from the ends 24 and 26 of vascular graft 20, it returns to the unstretched condition shown in FIG. 1.

Within FIG. 3, a cross section of vascular graft 20 is shown. Vascular graft 20 includes an inner expanded, porous PTFE tube having a micro-structure characterized by nodes interconnected by fibrils. PTFE tube 32 includes an inner cylindrical wall 34 and an opposing outer cylindrical wall 36. As shown in FIG. 3, outer cylindrical wall 36 is coated entirely around its circumference by a uniformly thick coating 38 of a biocompatible elastomer.

The preferred starting material used to form PTFE tube 32 is expanded porous PTFE material of the type generally described within U.S. Pat. No. 4,187,390 to Gore. Such expanded, porous PTFE material is commonly used to form prosthetic vascular grafts. The preferred Wall thickness of PTFE tube 32 ranges from 1 millimeter to 1.0 millimeters; the preferred internodal distance within such expanded PTFE material ranges from 10 micrometers to 60 micrometers. The longitudinal tensile strength of such PTFE material is preferably equal to or greater than 1500 psi, and the radial tensile strength of such PTFE material is preferably equal to or greater than 400 psi. The suture retention strength of such PTFE starting material is preferably equal to or greater than 300 grams.

In regard to elastomeric coating 38 shown in FIG. 3, such elastomeric coating is selected to be a biocompatible elastomer and may be selected from the group consisting of medical-grade silicone rubber elastomers, segmented polyurethanes, polyurethane-ureas, and silicone-polyurethane copolymers. Suitable candidates for use as elastomeric coating 38 typically have a hardness rating between 50A-100A and 55D-60D. Most of the above-mentioned elastomers can be chemically or biologically modified to improve biocompatability; such modified compounds are also candidates for use in forming elastomeric coating 38 shown in FIG. 3.

Apart from biocompatability, other requirements of an elastomer to be a suitable candidate for use as elastomeric coating 38 are that the elastomer be sufficiently elastic to maintain compressed portions of PTFE tube 32 in the compressed condition when vascular graft 20 is not being stretched. The elastomer should also be sufficiently elastic to effect instantaneous closure of suture holes formed by a suture needle. Elasticity should be balanced against the thickness of elastomeric coating 38, the objective being to select the minimum coating thickness necessary to prevent significant blood leakage through the suture hole locations without significantly impeding suture needle penetration. Yet another requirement of such elastomers is that they be easily dissolvable in low boiling point organic solvents such as tetrahydrofuran, methylene chloride, trichloromethane, dioxane, and dimethylformamide, by way of example. Finally, suitable elastomers should lend themselves to application to PTFE tube 32 by either the dip coating or spray coating methods described in greater detail below.

The presently preferred elastomer used to form elastomeric coating 38 is a polyurethane formulation grade SG-80 sold under the trademark "TECOFLEX" by Thermedics, Inc. of Woburn, Mass. Such formulations are considered medical grade aliphatic polyurethanes resins of solution processible grades. Such formulations are designed to be dissolved in various solvents for use in solution casting or for coating of medical products. The polyurethane formulation is preferably dissolved in the solvent known as Tetrahydrofuran (THF), a solvent commercially available from Mallinckrodt, Inc through the Scientific Products Division of Baxter Corp., of Irvine, Calif.

Further details concerning the preferred construction of vascular graft 20 shown in FIGS. 1-3 can more readily be understood in conjunction with the preferred method by which vascular graft 20 is produced. It has already been noted above that PTFE tube 32 is formed of expanded, Porous PTFE material of a type often used to form vascular prostheses. In practicing the preferred method, the PTFE starting material is initially in the form of a cylindrical tube having an inside diameter ranging from 1.0 millimeters to 30 millimeters, and ranging in length up to 100 centimeters.

As mentioned above, the PTFE tube starting material is compressed along the longitudinal axis of the PTFE tube prior to application of the elastomeric coating to the outer cylindrical wall of the PTFE tube. The preferred manner of compressing the PTFE tube starting material will now be described in conjunction with FIGS. 4-6. Within FIGS. 4-6, the PTFE tube starting material is designated by reference numeral 66. As shown in FIG. 4, PTFE tube 66 is pulled over a cylindrical supporting mandrel 68 which has an outer diameter that is equal to or slightly larger than the internal diameter of PTFE tube 66. Preferably, mandrel 68 should be approximately 0.2-0.4 millimeters larger than the inside diameter of PTFE tube 66 to prevent PTFE tube 66 from sliding, which sliding might result in a non-uniformly compressed graft.

The compression procedure is shown in FIG. 5 and may be accomplished by manually squeezing PTFE tube 66 from both of its ends until a predetermined final compressed length is reached, as shown in FIG. 5. The preferred compression ratio, defined as the ratio of the final compressed length shown in FIG. 5 to the initial uncompressed length shown in FIG. 4, is 0.5-0.6, but may vary between 0.3-0.9 depending upon the expansion ratios which were used when manufacturing the PTFE tube starting material, and depending upon the intended use of the final product. The appearance of the compressed PTFE tube 66 in FIG. 5 is nearly the same as that of the uncompressed PTFE tube 66 shown in FIG. 4, except that the compressed tube wall is more dense. Visually, the compressed PTFE tubing is no different from the original uncompressed tubing; no folding or wrinkling of PTFE tube 66 occurs, since the porous wall structure thereof easily allows compression back to the starting length (not shown) of the PTFE tube structure before it was expanded during the manufacturing process to form a porous tube.

The assignee of the present invention has long marketed PTFE vascular grafts having a pair of blue lines extending longitudinally along the PTFE graft upon the outer cylindrical wall thereof. In performing the compression procedure shown in FIG. 5, it was noted that the aforementioned blue lines become somewhat darker in color as PTFE tube 66 is compressed. One method of determining the uniformity of the compression procedure shown in FIG. 5 is to visually check the color density of the aforementioned blue lines throughout the length of the compressed PTFE tube 66.

As shown in FIG. 6, once PTFE tube 66 has been uniformly compressed along its length, it is held in place upon mandrel 68 by a pair of brass wires 62 and 64 which are tied about the ends of compressed PTFE tube 66. The end portions secured by brass wire 62 and 64 are subsequently trimmed off during quality control procedures after the manufacture of the vascular graft be completed.

Following the aforementioned compression process, the above-described elastomeric coating may then be applied to the outer cylindrical wall of compressed PTFE tube 66. As mentioned above, the two preferred methods of applying the elastomeric coating are dip coating and spraying. Regardless of which application method is used, the preferred method of formulating the liquified elastomer is the same. As has been described, the preferred liquified elastomer is formed by preparing a solution of "Tecoflex" polyurethane grade SG-80A. This solution is prepared by dissolving polyurethane pellets in the above-described tetrahydrofuran solvent in a heated glass reactor equipped with a cold water condenser held at 60° C. Such polyurethane pellets may also be dissolved in the solvent at room temperature through continuous stirring. The use of the heated reactor is preferred, as it dissolves the polyurethane pellets in a few hours, whereas the method of stirring the solution at room temperature takes approximately two days.

The preferred solids content for "Tecoflex" grade SG-80A is 2–4 by weight; however, the solids content may range up to 15 percent by weight, depending upon the specific polymer composition, the dip coating parameters, and the intended end uses. Where multiple coatings are employed, the composition of the polyurethane solution may be varied between coating layers. For example, it might be advantages to apply progressively more dilute polyurethane solutions to the underlying PTFE tube.

Following preparation of the liquified polyurethane solution as described above, the next step is to apply the polyurethane solution as a coating upon the outer wall of compressed PTFE tube 66. The method of dip coating the compressed PTFE tube will now be described in conjunction with FIG. 7, which illustrates a dip coating machine.

FIG. 7 illustrates a dip coating machine designated generally by reference numeral 65. As mentioned above, mandrel 68 is preferably selected to have a diameter that is approximately 0.2–0.4 millimeters larger than the inside diameter of PTFE tube 66 to prevent PTFE tube 66 from sliding upon mandrel 68 during the coating process. Preferably, the compressed length of PTFE tube 66 is approximately 25–30 centimeters. Lengths in excess of 30 centimeters are not preferred due to the effects of gravity pulling upon the polyurethane coating during the coating process; attempts to process compressed PTFE tube sections much in excess of 25–30 centimeters in length can result in uneven coating thicknesses as measured between the top and bottom of mandrel 68.

As shown in FIG. 7, mandrel 68 extends vertically downward from a motor 70 Which continuously rotates mandrel 68 and compressed PTFE tube 66 secured thereto. Motor 70 is, in turn, supported by a bracket 72 adapted to travel vertically upward and downward. Bracket 72 includes a smooth bushing 74 through Which a smooth vertical support rod 76 passes. Bushing 74 is adapted to slide upwardly and downwardly along support rod 76. Bracket 72 further includes a threaded collar 78 through which a threaded rotatable drive rod 80 passes. The lowermost end of drive rod 80 is secured to the drive shaft of a second motor 82 which rotates in a first rotational direction to raise mandrel 68 and which rotates in an opposing rotational direction to lower mandrel 68. Both motor 82 and support rod 76 are supported at their lower ends by a base 84. The upper end of support rod 76 is fixedly secured to bracket 86 which rotatably supports the upper end of drive rod 80.

Motor 82 of dip coating machine 65 is initially operated to raise mandrel 68 to its uppermost position. A tall, slender container 88 containing the above-described polyurethane solution 90 is placed upon base 84 immediately below mandrel 68. Motor 82 may then be operated in the reverse rotational direction to lower mandrel 68, and PTFE tube section 66 secured thereto, into polyurethane solution 90.

The variables controlled by dip coating machine 65 include the speed at which mandrel 68 is immersed and withdrawn, the rotational speed of mandrel 68, and the drying time between successive coatings. These parameters are controlled to ensure that the polymer coating penetration is restricted to the outer layers of the PTFE tube section 66.

The preferred number of polyurethane solution coatings applied to compressed PTFE tube 66 is eight, but may range between one and twenty coatings, depending upon the concentration of the elastomer solution used in the dipping process, and depending upon the intended use of the end product. The preferred coating thickness at the completion of the dip coating process is between 0.06–0.08 millimeters, but may vary up to two millimeters, depending upon the dimensions of the coated tube and the elastomer solution concentration.

The dip coating procedure of immersing and then withdrawing compressed PTFE tube 66 is a continuous process, and compressed PTFE tube 66 is continuously in motion at any given time during the procedure. Drying intervals between successive polyurethane coatings can vary up to a few hours depending upon the type of solvent used and the drying conditions. Compressed PTFE tube 66 is dried in ambient air, preferably in an inert atmosphere, but may also be dried at elevated temperatures of 40°–100° C. Compressed PTFE tube 66 remains secured to mandrel 68 until the coating and drying process described above is completed. When the last of the eight coatings has substantially dried, compressed FTFE tube 66 is further dried under vacuum at 50° C. at 10–15 mmHg vacuum for 10–24 hours to completely remove any remaining solvents. The polyurethane coated compressed PTFE tube is then removed from mandrel 68, and the end portions previously secured by brass Wires 62 and 64 are trimmed off.

A second method for applying the polyurethane coating to the PTFE tube involves the use of spraying and Will now be described in conjunction with the spray coating machine shown in FIG. 8. The polyurethane solution to be sprayed is first prepared in the same manner as described above for the dip coating process. The polyurethane solution is inserted within cylinder 92 of a pump 94 for delivery through a plastic tube 96 to a spray nozzle 98. An inert gas, such as nitrogen, is also supplied to spray nozzle 98 through connecting tube 100 from supply tank 102. An inert gas is preferably used to minimize reactions which polyurethane can undergo upon exposure to air and oxygen.

Figure 8:
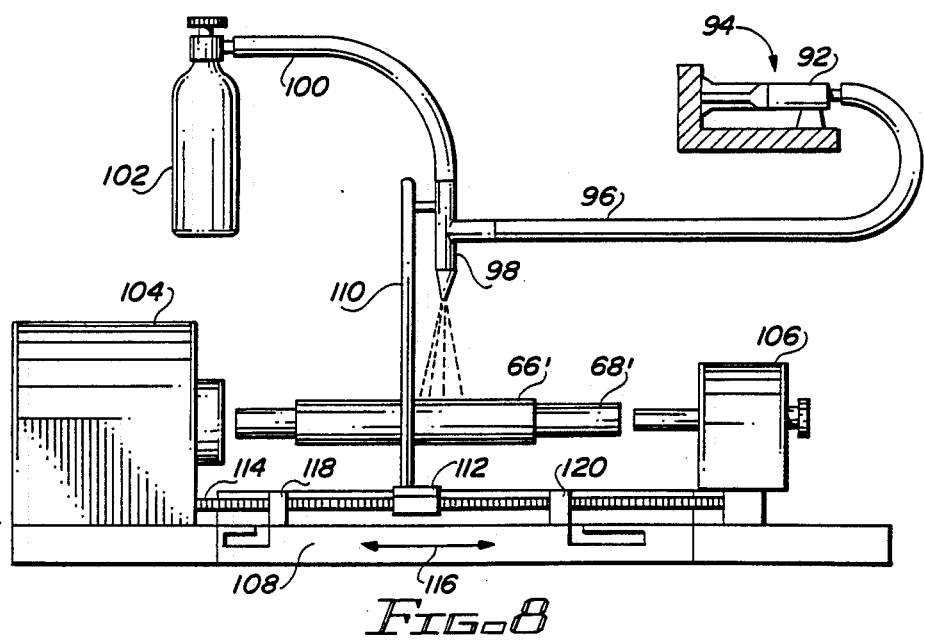
FIG. 8 is a front view of a spray coating apparatus which may be used to spray a liquified elastomer upon the outer cylindrical wall of a compressed PTFE tube to form a uniform elastomeric coating thereupon.

Still referring to FIG. 8, compressed PTFE tube 66' is again stretched over a mandrel 68'. Once again, mandrel 68' is preferably of a diameter slightly larger than the inner diameter of compressed PTFE tube 66' to prevent compressed PTFE tube 66' from sliding thereupon. Mandrel 68' is supported for rotation about a horizontal axis. One end of mandrel 68' is coupled to the drive shaft of a first motor (not shown) within motor housing 104, while the opposite end of mandrel 68 is rotatably supported by bracket 106. Both motor housing 104 and bracket 106 are supported upon base 108. The aforementioned first motor continuously rotates mandrel 68' at speeds of up to 500 rotations per minute.

Spray nozzle 98 is supported for reciprocal movement above and along mandrel 68'. As shown in FIG. 8, spray nozzle 98 is secured to support rod 110 which includes at its lowermost end a carriage 112. A threaded drive rod 114 is coupled at a first end to the drive shaft of a second motor (not shown) within motor housing 104 for being rotated thereby. The opposite end of threaded drive rod 114 is supported by and freely rotates within bracket 106. Threaded drive rod 114 threadedly engages a threaded collar (not shown) Within carriage 112. Accordingly, rotation of drive rod 114 causes carriage 112, and hence spray nozzle 98, to move in the directions designated by dual headed arrow 116, depending upon the direction of rotation of drive rod 114. Also shown in FIG. 5 are a pair of micro switches 118 and 120 Which are periodically engaged by carriage 112 and which, when actuated, reverse the direction of rotation of threaded drive rod 114 in a manner Which causes spray nozzle 98 to reciprocate back and forth along mandrel 68'.

As shown in FIG. 8, spray nozzle 98 makes several passes along mandrel 68', repetitively spraying compressed PTFE tube 66' as it rotates. Spray nozzle 98 is caused to travel at a linear speed of up to 50 centimeters per minute. The polyurethane coating thickness which results from this spraying process is determined by the speed of rotation of mandrel 68', the linear speed of spray nozzle 98, the concentration of polyurethane solution, as well as the rates of delivery of both the polyurethane solution by pump 94 and the rate of delivery o inert gas. These rates of delivery may range up to 5 milliliters per minute for the polyurethane solution, and up to 5 liters per minute for the nitrogen gas. After an appropriate number of spray cycles, the compressed PTFE tube 66' is vacuum dried, pulled from mandrel 68', and the end portions are trimmed, all in the same manner as described above.

Figure 10:
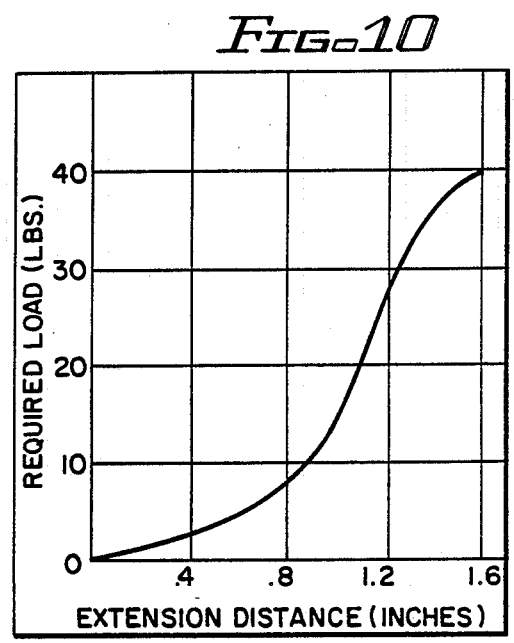
FIG. 10 is a graph illustrating a typical load-extension curve which indicates the extension distance typically observed for such a longitudinally compliant PTFE vascular graft as compared with the load, or force, applied to stretch apart the ends of the graft.

As mentioned above, the extreme end portions of the polyurethane coated PTFE tube may be trimmed off at the completion of the coating and drying steps. These trimmed end portions may be used as test samples to determine the uniformity of compression of the PTFE tube. Shown in FIG. 10 is a load-extension curve showing the amount of force or load which must be applied to cause a typical sample of a longitudinally compliant PTFE vascular graft to be stretched or extended by a given distance. With FIG. 10, the horizontal axis indicates the extension distance in inches, While the vertical axis indicates the required load or force, in pounds, to cause such extension. The aforementioned test samples trimmed from the polyurethane-coated compressed PTFE tube may be tested and compared to a typical load-extension curve to determine Whether both ends of the tube are Within required tolerance limits.

Figure 11:
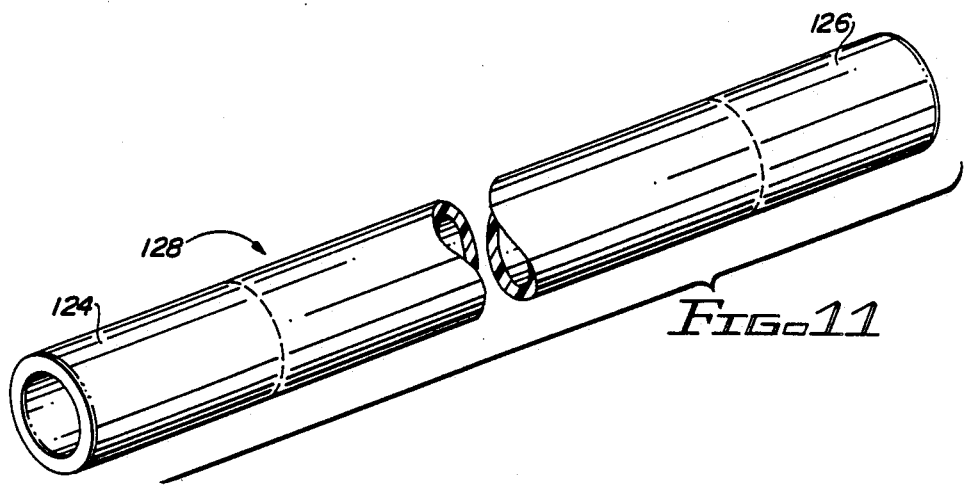
FIG. 11 illustrates a longitudinally compliant PTFE vascular graft wherein only the end portions thereof exhibit longitudinal compliance.

While the compression process described above in conjunction with FIGS. 4-6 is adapted to uniformly compress the PTFE tube along its entire length for producing a vascular graft that stretches along its entire length, those skilled in the art will appreciate that the regions of the PTFE tube that are to be compressed may be localized. For example, it may be desired to provide a vascular graft like that shown in FIG. 11 wherein only the opposing end portions 124 and 126 of vascular graft 128 are to be longitudinally elastic. In this instance, it should be understood that the compressive forces applied to PTFE tube 66 in FIGS. 4 and 5 may be localized to the end portions 124 and 126 (see FIG. 11), whereby only end portions 124 and 126 will be longitudinally elastic following the aforementioned coating and drying operations. Alternatively, the compressive forces applied to PTFE tube 66, shown in FIGS. 4 and 5, may be localized to the central region of PTFE tube 66, whereby only the central portion of the resulting vascular graft exhibits longitudinal elasticity.

While the dip coating and spray coating methods described above in conjunction with FIGS. 7 and 8 are directed to the process of coating the entire outer cylindrical wall of the compressed PTFE tube, those skilled in the art will appreciate that such dip coating and spray coating methods may be used to form an elastomeric coating upon only portions of the PTFE tube, particularly if less than the entire PTFE tube is being compressed, as it is usually necessary to coat only those portions of the PTFE tube which are compressed. For example, in the manufacture of the vascular graft product shown in FIG. 11 wherein only the end portions 124 and 126 are longitudinally elastic, it is not necessary to coat the central region of the PTFE tube With the liquified elastomer. Accordingly, the dip coating process illustrated in FIG. 7 may be practiced by dipping only one end of PTFE tube 66 into the liquified polyurethane solution 90; after the desired number of coatings have been applied to the lower end of PTFE tube 66, mandrel 68 may be inverted to cause the opposite end of PTFE tube 66 to be immersed within polyurethane solution 90. Similarly, in FIG. 8, spray nozzle 98 may be maintained away from the central region of PTFE tube 66' to avoid spraying such central region with the liquified elastomer. Alternatively, a cylindrical shield (not shown) may be extended around the central portion of PTFE tube 66' within the spray coating apparatus of FIG. 8 to prevent the liquified polyurethane spray from contacting the central region of PTFE tube 66'.

Figure 9:
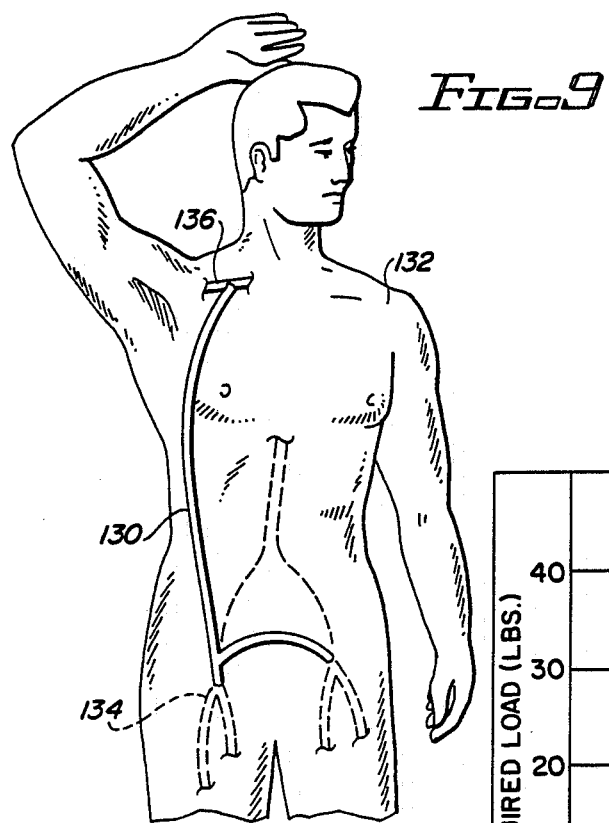
FIG. 9 illustrates, in outline form, the implantation of such a longitudinally compliant vascular graft within a patient's body to provide an axillofemoral bypass graft.

In FIG. 9, the use of a longitudinally compliant PTFE vascular graft is illustrated. Longitudinally compliant PTFE graft 130 has been implanted within patient 132 to provide an axillofemoral bypass graft. The lower end of vascular graft 130 is shown anchored to femoral artery 134, while the upper end of vascular graft 130 is shown anchored to axillary artery 136. When conventional, noncompliant PTFE grafts are used to perform such a bypass, the raising of arm 138, as shown in FIG. 9, places tension on graft 130, and places stress upon the sutured ends of graft 130, sometimes causing such ends to pull loose from the points at which they have been anastomosed to the aforementioned arteries. In contrast, the use of longitudinally compliant vascular graft 130 in such applications permits the graft to be stretched without imparting undue stress upon the anchored ends, thereby permitting the patient greater freedom of movement.

Those skilled in the art will now appreciate that an improved PTFE vascular graft has been described which is longitudinally compliant and which may be used wherever noncompliant PTFE prosthetic vascular grafts are currently used today, including various applications in both peripheral vascular and vascular access uses. The above-described longitudinally compliant graft may be implanted in the same manner as is currently used to implant noncompliant PTFE vascular grafts. Moreover, the elastomeric coating minimizes suture hole bleeding at the time of implantation, increases suture retention strength, reduces serious weepage, and inhibits tissue ingrowth. While the invention has been described with reference to preferred embodiments thereof, the description is for illustrative purposes only and is not to be construed as limiting the scope of the invention. Various modifications and changes may be made by those skilled in the art Without departing from the true spirit and scope of the invention as defined by the appended claims.

We claim:

1. A longitudinally compliant vascular graft comprising in combination:
   a. a length of porous PTFE tubing having a microstructure characterized by nodes interconnected by fibrils, said PTFE tubing having a central longitudinal axis and including an outer cylindrical wall, at least a portion of said PTFE tubing having been compressed along the central longitudinal axis thereof following the production of said PTFE tubing; and b. a coating of a biocompatible elastomer covering the outer cylindrical wall of said PTFE tubing over at least said compressed portion of said PTFE tubing;

c. said compressed portion of said PTFE tubing coated by said biocompatible elastomer being adapted to be stretched along the central longitudinal axis of said PTFE tubing.

2. A longitudinally compliant graft as recited by claim 1 wherein said coating of a biocompatible elastomer is a polyurethane coating.

3. A longitudinally compliant graft as recited by claim 1 wherein said biocompatible elastomer is selected from the group of elastomers consisting of medical-grade silicone rubber elastomers, segmented polyurethanes, polyurethane-ureas, and silicone-polyurethane copolymers.

4. A longitudinally compliant graft as recited by claim 1 wherein said coating of a biocompatible elastomer is a non-porous coating.

5. A method of producing a longitudinally compliant PTFE vascular graft which is adapted to be stretched along its longitudinal axis, said method comprising the steps of:

a. providing a porous PTFE tube having a predetermined internal diameter and having a longitudinal axis, and including an outer cylindrical wall;

b. compressing at least a portion of the tube along its longitudinal axis while maintaining the predetermined internal diameter of the tube substantially constant;

c. applying a coating of a liquified elastomer to the outer cylindrical wall of the tube over at least the compressed portion thereof; and d. drying the coating of liquified elastomer upon the outer cylindrical Wall of the tube while maintaining the compressed portion of the tube in a compressed condition.

6. The method recited by claim 5 Wherein said compressing step includes the steps of:

a. pulling the PTFE tube over a cylindrical mandrel having an outer diameter of approximately the same dimension as the internal diameter of the PTFE tube; and b. compressing at least a portion of the PTFE tube along the longitudinal axis of the tube while the tube is supported by the mandrel.

7. The method recited by claim 6 wherein said coating step includes the step of dicoating at least the compressed portion of the PTFE tube into a container of the liquified elastomer while said PTFE tube is supported upon the mandrel.

8. The method recited by claim 6 wherein said coating step includes the step of spraying the liquified elastomer upon the outer cylindrical wall of the PTFE tube over at least the compressed portion of the PTFE tube while the PTFE tube is supported upon the mandrel.

9. The method recited by claim 5 wherein the elastomer is selected from the group of elastomers consisting of medical-grade silicone rubber elastomers, segmented polyurethanes, polyurethane-ureas, and silicone-polyurethane copolymers.

10. The method recited by claim 5 wherein the PTFE tube has first and second end portions, and wherein said compressing step compresses only the first and second end portions of the PTFE tube without compressing the central portion thereof extending between the first and second end portions.

11. The method recited by claim 10 wherein said coating step includes the step of applying a coating of the liquified elastomer to the entire outer cylindrical wall of the PTFE tube.

12. The method recited by claim 5 wherein said compressing step includes the step of compressing the PTFE tube uniformly along its entire length, and wherein said coating step includes the step of applying the liquified elastomer over the entire outer cylindrical Wall of the PTFE tube.

13. A longitudinally compliant vascular graft resulting from using the method comprising the steps of:

a. providing a porous PTFE tube having a predetermined internal diameter and having a longitudinal axis, and including an outer cylindrical wall;

b. compressing at least a portion of the tube along its longitudinal axis While maintaining the predetermined internal diameter of the tube substantially constant;

c. applying a coating of a liquified elastomer to the outer cylindrical wall of the tube over at least the compressed portion thereof; and d. drying the coating of liquified elastomer upon the outer cylindrical Wall of the tube while maintaining the compressed portion of the tube in a compressed condition.

14. The longitudinally compliant vascular graft recited by claim 13, wherein the compressing step of the method used to produce such graft includes:

a. pulling the FTFE tube over a cylindrical mandrel having an outer diameter of approximately the same dimension as the internal diameter of the PTFE tube; and b. compressing at least a portion of the PTFE tube along the longitudinal axis of the tube while the tube is supported by the mandrel.

15. The longitudinally compliant vascular graft recited by claim 14, wherein the coating step of the method used to produce such graft includes the step of dip coating at least the compressed portion of the PTFE tube into a container of the liquified elastomer while said PTFE tube is supported upon the mandrel.

16. The longitudinally compliant vascular graft recited by claim 14, wherein the coating step of the method used to produce such graft includes the step of spraying the liquified elastomer upon the outer cylindrical wall of the PTFE tube over at least the compressed portion of the PTFE tube while the PTFE tube is supported upon the mandrel.

17. The longitudinally compliant vascular graft recited by claim 14, wherein said elastomer is selected from the group of the elastomers consisting of medical-grade silicone rubber elastomers, segmented polyurethanes, polyurethane-ureas, and silicone-polyurethane copolymers.

18. The longitudinally compliant vascular graft recited by claim 13 wherein the PTFE tube has first and second opposing end portions and a central portion lying there between, and wherein the compressing step of the method used to produce such vascular graft includes the step of compressing only the first and second end portions of the PTFE tube without compressing the central portion thereof extending between the first and second end portions.

19. The longitudinally compliant vascular graft recited by claim 18 wherein the coating step of the method used to produce such vascular graft includes the step of applying a coating of the liquified elastomer to the entire outer cylindrical wall of the PTFE tube.

* * * * *